United States Patent [19]

Shafer et al.

[11] Patent Number: 5,163,993
[45] Date of Patent: Nov. 17, 1992

[54] GRAPE CLUSTER THINNING COMPOSITION AND METHOD

[75] Inventors: Warren E. Shafer, Libertyville; Bala N. Devisetty, Buffalo Grove, both of Ill.

[73] Assignee: Abbott Laboratories, Abbott Park, Ill.

[21] Appl. No.: 675,236

[22] Filed: Mar. 26, 1991
(Under 37 CFR 1.47)

Related U.S. Application Data

[63] Continuation-in-part of Ser. No. 442,088, Nov. 28, 1989, abandoned.

[51] Int. Cl.⁵ ............................................ A01N 43/08
[52] U.S. Cl. .................................... 71/89; 71/DIG. 1
[58] Field of Search ............................ 71/89, DIG. 1

[56] References Cited

U.S. PATENT DOCUMENTS 3,038,794  6/1962  Geary et al. ............................ 71/89
4,110,102  8/1978  Pharis ..................................... 71/89

FOREIGN PATENT DOCUMENTS 614151  2/1961  Canada .................................. 71/89

Primary Examiner—Richard L. Raymond
Assistant Examiner—Brian G. Bembenick
Attorney, Agent, or Firm—Steven F. Weinstock; Jerry F. Janssen

[57] ABSTRACT

A composition and method for thinning Perlette Seedless grape clusters is disclosed. The composition contains a surfactant and a gibberellin. In a method for thinning Perlette Seedless grape clusters, the composition is applied to Perlette Seedless grape clusters during bloom, with the result that clusters are produced that have fewer grapes and in which the grapes are increased in size and weight.

2 Claims, No Drawings

GRAPE CLUSTER THINNING COMPOSITION AND METHOD

This is a continuation-in-part of U.S. patent application Ser. No. 07/442,088, filed Nov. 28, 1989 (abandoned).

TECHNICAL FIELD

The present invention relates to compositions and methods that utilize a gibberellin and a surfactant for thinning Perlette Seedless grape clusters.

BACKGROUND OF THE INVENTION

Seedless table grapes are a commercially attractive commodity with high consumer demand. A common problem encountered in the production of these grapes is that they tend to grow as small berries in compact clusters, which results in berry rupture and bunch rot. Thinning of these clusters is necessary in order to reduce the occurrence of bunch rot and to allow the berries which remain an opportunity to increase in size. Both of these factors are important in terms of producing a commercially acceptable crop.

Several strains of seedless grapes exist, such as Thompson Seedless and Perlette Seedless. The Perlette Seedless table grape strain is an early-maturing variety. The mature fruit have a striking translucence, thus the name "Perlette" signifying "little pearl". The fruit clusters are distinct in the compactness and earliness of maturity. This latter aspect is the primary reason why Perlettes are of commercial significance. Perlette clusters are large, about 450 to 700 grams, and very compact. The spherical berries are covered with an abundant waxy bloom and have a pale gold color. The clusters tend to be overly compact and subject to rotting unless extensive thinning of the berries is undertaken. Without thinning, the mature berries are undersized and not commercially acceptable.

There is currently no chemical treatment that is commercially used to thin Perlette Seedless grape clusters. Thinning of Perlette Seedless grapes currently requires extensive hand-thinning, which is time consuming and expensive.

Gibberellins are chemicals that are naturally found in small amounts in all plant species, including grapes. They function as regulators of plant growth. Giberellins are obtained commercially by growing large cultures of Gibberella fungus in nutrient medium and then isolating the gibberellins from the liquid medium.

One of the principal effects of gibberellins on plants is to promote rapid growth and elongation of cells that are still growing or are capable of growth. Gibberellic acid has also been shown to increase fructification of fruit trees. Belgian Patent No. 756990. When applied on grapes post-bloom, these compounds can produce larger berries.

The use of surfactants is commonplace for many agricultural applications. Surfactants modify the physical:chemical characteristics of agricultural formulations. These modifications include: lower surface tensions, emulsification of formulation components, and increased wetting/retention of spray droplets on plant surfaces. Behrens, R. W., *Weeds*, (1964) 12:255–258.

While all surfactants are capable of the physical:chemical modifications described above, only a few surfactants also demonstrate biological activity in plant tissues. Parr et al. (1965) *Bot. Gaz.* 126:86–96. This tends to complicate the process of selecting the right surfactant for a particular use because the relationship between biological activity and surfactant chemistry/structure is not well understood. Foy, C. L., *Adjuvants and Aqrochemicals*, Vol. I; Chow et al. (1989), CRC Press, pp. 1–15; Matsui et al. (1989) *Proc. PGRSA Ann. Mtg.* pp 234–236. As it stands now, there is no way to accurately predict the biological activity of a surfactant in a given plant system.

Gibberellins have successfully been utilized to enhance berry size and reduce berry set in seedless grape cultures, particularly Thompson Seedless. Lynn et al, *Am. J. Enol. Viticult.*, 17:283–289 (1966); Dass et al., *J. Hort. Sci.*, 52:189–191 (1977). This is an accepted commercial practice.

The application of gibberellin together with a modified phthalic glycerol alkyd resin surfactant (Triton B-1956; Rohm and Haas Co., Philadelphia, Pa.) has been used effectively to thin clusters of Thompson Seedless grapes. Similar treatments with a $C_{10}$ to $C_{18}$ linear polyethoxylated alcohol surfactants have been carried out on a seedless variety of Kishmish black grapes utilizing gibberellin. Salenkov et al. (1984) *Puti Intensif. Vinocrad.*, pp. 66–71 (Puponin, A. E., ed., Mosk. S-kh. Akad.:Moscow, USSR). The gibberellin/surfactant composition was applied post-bloom and resulted in an increased yield of Kishmish grapes.

The application of gibberellic acid and a modified phthalic glycerol alkyd resin surfactant (e.g., Triton B-1956) to Perlette Seedless grape clusters has a variable effect on thinning, frequently demonstrating little or no significant thinning activity. The composition was applied to the Perlette Seedless grapes in California during bloom, and only minimal thinning was obtained. Kasimatis et al. *Am. J. Enol. Vitic.*, 22:19–23 (1971).

Several studies have been conducted in India on the effect of gibberellins upon thinning of Perlette Seedless grapes. The results of these studies have shown mixed effects. The application of gibberellic acid alone (i.e., no surfactant included) to Perlette Seedless grapes produced thinning as the gibberellic acid concentration increased, but the percentage of "shot" berries (i.e., berries which remain small and do not mature physiologically over the course of the growing season) also increased. Nijjar et al., *Indian J. Hort.*, 28:199–202 (1971); Dhillon et al., J. Res. Punjab Agric. Univ., 10:331–336 (1973). The presence of "shot" berries in a grape cluster is commercially unacceptable.

When gibberellic acid was combined with "soap" and applied to Perlette Seedless grape clusters, larger, heavierberries with a higher sugar/acid ratio were produced. Tripathi, *Punjab Hort. J.*, 8:60–64 (1967). The combination of gibberellic acid with dish soap (Teepol, National Organic Chemical Industries, Ltd., Bombay, India) and subsequent application to Perlette Seedless grapes during pre-bloom produced significant thinning of grape clusters; however, the percentage of "shot" berries doubled. Singh et al., *South Indian Hort.*, 33:330–332 (1985). In another study with combinations of gibberellic acid (at four different concentrations) and Teepol applied to Perlette Seedless grape clusters, three out of four treatments, including the lowest and highest gibberellic acid concentrations tested, showed no significant thinning activity. Sandhu et al., *Harvana J. Hort. Soc.*, 14:221–214 (1985). Application of gibberellic acid together with a surfactant (Triton) as a wetting agent significantly reduced the compactness of berries in Perlette Seedless grape clusters; however the percentage of "shot" berries tended to increase. Chaturvedi et al., Vitis, 18:10–16 (1979).

Because of this variable effect on thinning activity and "shot" berry development, gibberellic acid formulations are not currently used for commercial thinning of Perlette grapes. Instead, hand-thinning is used in commercial practice.

SUMMARY OF THE INVENTION

The present invention provides a composition and method that overcomes the difficulties reported in the art of thinning Perlette Seedless grape clusters.

A composition of the present invention contains a surfactant together with a gibberellin dissolved or dispersed in a liquid carrier. Not just any sufactant is acceptable however. A preferred surfactant is a polyethoxylated surfactant, such as trimethylnonylpolyethoxyethanol, a polyethoxylated derivative of octylphenol or nonylphenol, polyoxyethylene (20) sorbitan monolaurate or polyoxyethylene (20) sorbitan monooleate.

In a method of the present invention, an acceptable surfactant and a gibberellin are applied to Perlette Seedless grape flower clusters during the bloom period in order to consistently effect thinning of the clusters, as well as increase fruit size and eliminate the presence of "shot" berries. Only selected nonionic, anionic, cationic and amphoteric surfactants are useful in the method of the present invention. The preferred surfactants are a polyethoxylated surfactant, such as trimethylnonylpolyethoxyethanol, a polyethoxylated derivative of octylphenol or nonylphenol, polyoxyethylene (20) sorbitan mono-laurate or polyoxyethylene (20) sorbitan monooleate.

DESCRIPTION OF PREFERRED EMBODIMENTS

The present invention is directed to a composition and a method for thinning Perlette Seedless grape clusters.

The composition of the present invention contains a gibberellin, such as gibberellic acid ($GA_3$), at a concentration of about 5 to about 25 parts per million, together with an acceptable surfactant at a concentration of about 0.1 to about 1.0 percent weight by volume (w/v).

As used herein, "surfactant" refers to certain nonionic, anionic, cationic and amphoteric surfactants. Preferred surfactants include trimethylnonylpolyethoxyethanol, as is commercially available as Surfactant WK (DuPont Company, Inc., Wilmington, Del.), or polyethoxylated derivatives of octylphenol or nonylphenol, such as nonylphenoxypolyethoxyethanol, as is commercially available as the Triton X or N series (Rohm and Haas Co., Philadelphia, Pa.), and Igepal CA and CO series (GAF Corporation, Wayne, N.J.), or polyoxyethylene (20) sorbitan monolaurate and polyoxyethylene (20) sorbitan monooleate, as are commercially available as Tween 20 and Tween 80, respectively (ICI Americas Inc., Wilmington, Del.). Additional surfactants useful for thinning include Silwet L-77 (nonionic; polyalkyleneoxide modified polydimethylsiloxane, Union Carbide, NY, N.Y.), Aerosol TO-100 (anionic; sodium dioctyl sulfosuccinate, sulfosuccinate, American Cyanamid, Wayne, N.J.), Mazeen C-5 (cationic; polyoxyethylene (5) coco amine, Mazer Chemicals, Ltd., Gurnee, Ill.), and Mafo CB40 (amphoteric; coco betaine, Mazer Chemicals, Ltd.). The remainder of the composition can comprise an organic solvent, such as isopropanol or tetrahydrofuryl alcohol, at a concentration of about 0.1 to 1.0 percent weight volume (w/v), and water.

As used herein, a "gibberellin" refers to a cyclic diterpenoid acid plant hormone that stimulates growth in plants. The gibberellins are derived from the tetracyclic entgibberellane skeleton. Over 70 gibberellins have been characterized and are identified using the nomenclature $GA_1$, $GA_2$, $GA_3$, etc. The gibberellins are of widespread occurrence and are found in bacteria, algae, mosses, ferns, gymnosperms, and angiosperms. The gibberellins are generally found in small amounts, with the exception of the fungus *Gibberel fujikuroi* and the immature seeds of some plants which are rich sources of gibberellins. The gibberellins play an important role in the integration of growth and development of plants. The present invention may also include glucoside and glucose ester conjugates of gibberellins.

As used herein, "grape cluster" refers to a compact arrangement of Perlette Seedless grapes. When clusters are very compact, rotting occurs because of trapped moisture within the cluster or berry splitting. Thinning of grape clusters is necessary to produce commercially acceptable grapes.

As used herein, the term "liquid carrier" refers to a nontoxic liquid medium, such as water, in which a surfactant and gibberellin of the present invention can be dissolved or dispersed for application to grape clusters and vines. Illustrative liquid carriers also include tetrahydrofuryl alcohol, dimethylsulfoxide, isopropanol, methanol, and ethanol.

As used herein, the term "bloom period" refers to the period during which any Perlette Seedless grapes in a cluster on the grapevine begin to flower.

The present invention is directed to a method for thinning Perlette Seedless grape clusters by applying to the clusters at bloom, a gibberellin together with an acceptable surfactant such as trimethylnonylpolyethoxyethanol, a polyethoxylated derivative of octylphenol or nonylphenol surfactant, polyoxyethylene (20) sorbitan monolaurate or polyoxyethylene (20) sorbitan monooleate. Application can be by any means, and preferably is by spraying a gibberellin/surfactant composition onto grape clusters, vines, or both. In a preferred embodiment, the Perlette Seedless grape clusters are sprayed twice during bloom to run-off, which results in the total application of about 15 grams of gibberellin per acre.

The method of treating Perlette Seedless grape clusters of the present invention allows for the development of large mature grapes over the course of the growing season, and did not result in the production of small, immature "shot" berries. The lack of significant "shot" berry formation was consistently observed with respect to all EXAMPLES following the treatments of Perlette Seedless grape clusters with the compositions of the present invention, as hereinafter described.

The present invention is further illustrated by the following EXAMPLES, which are not intended to be limiting.

EXAMPLE 1

Treatment compositions containing 20 ppm $GA_3$, either alone or in combination with 0.5 percent Triton B-1956 were applied to tagged clusters of Perlette Seedless grapes (eight clusters/group) using a $CO_2$ backpack sprayer. The treatment compositions were prepared by first dissolving $GA_3$ in tetrahydrofuryl alcohol, followed by adding the dissolved $GA_3$ to water. The surfactant was then added to the solution and additional water was added to produce a final volume of 1 liter. The surfactant is preferably added to the solution prior to adjusting the volume with water in order to avoid solubility problems that can arise with some surfactants.

The compositions were applied during the period of 30 to 70 percent full bloom, and the compositions were sprayed onto the clusters to run-off. Hand-thinned Perlette Seedless grape clusters were used as a control. Data, collected at harvest, are shown in Table I.

TABLE I

| Treatment | # Normal Berries per cm lateral | Percent of UTC |
|---|---|---|
| Untreated control (UTC) | 4.9 (1.3)[z] | 100 |
| 20 ppm $GA_3$ | 5.3 (1.3) | 108 |
| 20 ppm $GA_3$ + 0.5 percent Triton B-1956 | 5.0 (1.2) | 101 |
| Hand-thinned control | 3.6 (1.3) | 73 |

[z]mean of 10 to 16 laterals ($2^{nd}$ and $3^{rd}$ true laterals taken from 5 to 8 clusters) with standard deviations in parenthesis.

The results shown in Table I illustrate that neither $GA_3$ alone or $GA_3$+Triton B-1956 (modified phthalic gylcerol alkylated surfactant; the traditional spray tank formulation used in the grape industry) are effective Perlette thinning treatments.

EXAMPLE 2

Perlette Seedless grape clusters were treated as described in EXAMPLE 1, using the compositions shown in Table II, at a bloom stage about 50-100 percent full bloom. The results are shown in Table II.

TABLE II

| Treatment | # Normal Berries per cm lateral | Percent of UTC |
|---|---|---|
| Untreated control (UTC) | 5.5 (1.0)[z] | 100 |
| 20 ppm $GA_3$ | 3.1 (0.7) | 56 |
| 20 ppm $GA_3$ + 1.0 percent Surfactant WK | 1.7 (1.3) | 31 |
| 20 ppm $GA_3$ + 1.0 percent Silwet L-77 | 2.4 (0.2) | 44 |
| Hand-thinned control | 2.7 (0.5) | 49 |

[z]means of 4 to 8 laterals ($2^{nd}$ and $3^{rd}$ true laterals taken from 2 to 4 clusters) with standard deviations in parentheses.

The results shown in Table II illustrate that combinations of $GA_3$ and either 1 percent Surfactant WK (trimethylnonylpolyethoxyethanol) or 1 percent Silwet L-77 (polyalkyleneoxide modified polydimethylsiloxane) demonstrated greater thinning activity (i.e., less berries per cm lateral) than $GA_3$ alone. The level of thinning was in both instances more than obtained with the hand-thinned control.

The fact that $GA_3$ by itself showed thinning activity in one experiment (Table II) but not in another (Table I; see also Table III below) is typical of previously published reports. These data underscore the variability one obtains by using $GA_3$ to thin Perlettes, which is the reason why this treatment is not practiced commercially.

EXAMPLE 3

Perlette Seedless grape clusters were treated as described in EXAMPLE 1. The treatment compositions and results are shown in Table III.

TABLE III

| Treatment | # Normal Berries per cm lateral | Percent of UTC |
|---|---|---|
| Untreated control (UTC) | 4.3 (0.9)[z] | 100 |
| 20 ppm $GA_3$ | 4.6 (0.9) | 107 |
| 20 ppm $GA_3$ + 0.5 percent Surfactant WK | 3.8 (0.6) | 88 |
| 20 ppm $GA_3$ + 1.0 percent Surfactant WK | 3.2 (1.1) | 74 |
| Hand-thinned control | 2.5 (0.4) | 58 |

[z]mean of 8 to 9 laterals (2nd and 3rd true laterals taken from 4 to 5 clusters) with standard deviations in parentheses.

These results show that the combination of $GA_3$ with Surfactant WK decreases the number of grapes per cluster better than $GA_3$ alone, and that thinning of Perlette Seedless grapes is dependent upon the concentrations of Surfactant WK.

The results shown in Table III illustrate that $GA_3$ alone showed no thinning activity, compared to the untreated control. Perlette thinning was obtained only when $GA_3$ was combined with Surfactant WK surfactant (trimethylnonylpolyethoxyethanol; 0.5 or 1.0 percent).

EXAMPLE 4

Perlette Seedless grape clusters at 30-80 percent of full bloom were treated as described in EXAMPLE 1. The treatment compositions and results are shown in Table IV.

TABLE IV

| Treatment | # Normal Berries per cm lateral | Percent of UTC |
|---|---|---|
| Untreated control (UTC) | 3.9 (2.0)[z] | 100 |
| 20 ppm $GA_3$ + 0.5 percent Triton X-100 | 2.5 (0.9) | 64 |
| 20 ppm $GA_3$ + 0.75 percent Triton X-100 | 1.8 (0.6) | 46 |
| 20 ppm $GA_3$ + 1.0 percent Triton X-100 | 1.1 (0.7) | 28 |
| 20 ppm $GA_3$ + 0.1 percent Triton N-101 | 2.2 (1.3) | 56 |
| 20 ppm $GA_3$ + 1.0 percent Triton N-101 | 1.6 (0.8) | 41 |
| Hand-thinned control | 2.1 (0.7) | 54 |

[z]mean of 8 to 14 laterals ($2^{nd}$ and $3^{rd}$ true laterals taken from 4 to 7 clusters) with standard deviations in parentheses.

The results shown in Table IV illustrate that Triton X-100 and Triton N-101 (octylphenoxypolyethoxyethanol and nonylphenoxypolyethoxyethanol, respectively, Rohm and Haas, Philadelphia, Pa.) are also effective, when combined with $GA_3$, in thinning Perlette clusters. In addition, the data show that the degree of thinning activity obtained with $GA_3$/Triton X-100 or $GA_3$/Triton N-101 combinations is dependent on Triton X-100 or Triton N-101 concentration.

EXAMPLE 5

Perlette Seedless grape clusters were treated with 20 ppm $GA_3$ and 1 percent surfactant as described in EXAMPLE 1. The treatment compositions and results are shown in Table V.

TABLE V

| Treatment | # Normal Berries per cm lateral | Percent of UTC |
|---|---|---|
| Untreated control (UTC) | 3.9 (2.0)[z] | 100 |
| 20 ppm $GA_3$ + 1.0 percent Triton X-45 | 0 | 0 |
| 20 ppm $GA_3$ + 1.0 percent | 1.3 (0.9) | 35 |

TABLE V-continued

| Treatment | # Normal Berries per cm lateral | Percent of UTC |
|---|---|---|
| Triton X-114 | | |
| 20 ppm GA$_3$ + 1.0 percent Triton X-100 | 1.1 (0.6) | 28 |
| 20 ppm GA$_3$ + 1.0 percent Triton X-102 | 1.6 (1.2) | 41 |
| Hand-thinned control | 2.1 (0.7) | 54 |

$^z$mean of 8 to 14 laterals (2$^{nd}$ and 3$^{rd}$ true laterals taken from 1 to 7 clusters) with standard deviations in parentheses.

The results shown in Table V illustrate that oxtylphenoxypolyethoxyethanol surfactants differing only in their polyxyethylene (POE) content (POE content for Tritons X-45, X-114, X-100 and X-102 are 5, 7.5, 9.5 and 12.5 ethylene oxide units per molecule, respectively), have varying levels of thinning activity when combined with GA$_3$.

EXAMPLE 6

Perlette Seedless grape clusters were treated with 10 ppm GA$_3$ either alone or together with 0.5 percent surfactant. The surfactants studied represented nonionic, anionic, cationic and amphoteric surfactants. The grape clusters were treated as described in EXAMPLE 1. The treatment compositions and results are shown in Table VI.

TABLE VI

| Treatment$^z$ | # Normal Berries Per cm lateral | Percent of UTC |
|---|---|---|
| Untreated control (UTC) | 4.9 (1.3)$^y$ | 100.0 |
| GA$_3$ Only | 5.3 (1.3) | 108.2 |
| NONIONIC | | |
| GA$_3$ + 0.5 percent Igepal CO-630 | 4.8 (1.8) | 98.0 |
| GA$_3$ + 0.5 percent Macol LA-790 | 4.3 (1.7) | 87.8 |
| GA$_3$ + 0.5 percent Macol OA10 | 6.2 (1.3) | 126.5 |
| GA$_3$ + 0.5 percent Macol OP+8 | 6.1 (1.6) | 124.5 |
| GA$_3$ + 0.5 percent Mapeg 200 ML | 4.9 (1.1) | 100.0 |
| GA$_3$ + 0.5 percent Mapeg 400 ML | 5.2 (1.4) | 106.1 |
| GA$_3$ + 0.5 percent Mazol 159 | 4.7 (1.6) | 95.9 |
| GA$_3$ + 0.5 percent Silwet L-77 | 3.2 (1.1) | 63.3 |
| GA$_3$ + 0.5 percent S-Maz-20 | 5.2 (2.5) | 106.1 |
| GA$_3$ + 0.5 percent T-Maz-20 | 4.3 (1.9) | 87.8 |
| ANIONIC | | |
| GA$_3$ + 0.5 percent Aerosol OT-100 | 3.7 (1.3) | 75.5 |
| GA$_3$ + 0.5 percent Avanel S-74 | 4.6 (1.7) | 93.9 |
| GA$_3$ + 0.5 percent Triton QS-44 | 4.5 (1.7) | 91.8 |
| CATIONIC | | |
| GA$_3$ + 0.5 percent Mazeen C-5 | 2.0 (1.2) | 40.8 |
| GA$_3$ + 0.5 percent Toximul TA-20 | 4.5 (1.0) | 91.8 |
| AMPHOTERIC | | |
| GA$_3$ + 0.5 percent Mafo CB-40 | 3.4 (0.9) | 69.4 |
| OTHER | | |
| GA$_3$ + 0.5 percent Nu-Film-17 | 5.1 (0.6) | 104.1 |

TABLE VI-continued

| Treatment$^z$ | # Normal Berries Per cm lateral | Percent of UTC |
|---|---|---|
| Hand Thinned (HT) Control | 3.6 (1.3) | 73.5 |

$^z$Surfactants were commercially obtainable from:
GAF Corp., Wayne, NY:
Igepal CO-630
Mazer Chemicals Ltd., Gurnee, IL:
Macol LA 790 (polyethoxylated lauryl alcohol).
Macol OA 10 (polyethoxylated oleyl alcohol).
Macol OP+8 (polyethoxylated (8) octylphenol).
Mazol 159 (polyethylene glycol (7) glycerol cocoate).
Mapeg 200 ML (polyethylene glycol (200) monolaurate).
Mapeg 400 ML (polyethylene glycol (400) monolaurate),
S-Maz-20 (sorbitan monolaurate),
T-Maz-20 (polyoxyethylene sorbitan (20) monolaurate,
Avanel S-74 (sodium linear alkylpolyether sulfonate),
Mazeen C-5 (polyoxyethylene(5)coco amine), and
Mafo CB-40 (coco betaine)
Union Carbide Corp., Danbury, CT.:
Silwet L-77 (polyalkyleneoxide modified polydimethylsiloxane)
Rohm and Haas, Philadelphia PA:
Triton QS-44 (octylphenoxypolyethoxyethyl phosphate surfactant in free acid form)
American Cyanamid, Wayne, NJ:
Aerosol OT-100 (sodium dioctyl sulfosuccinate)
Stepan Co., Northfield, IL:
Toximul TA-20 (tallow amine ethoxylate)
Miller Chemical Co., Chigaco, IL:
Nu-Film 17 (Di-1-p-methene)
$^y$Means of 8 to 16 total laterals (2$^{nd}$ and 3$^{rd}$ laterals taken from 4 to 8 clusters) with standard deviation in parentheses.

The results shown in Table VI illustrate representatives from the four ionogenic surfactant classes (i.e., nonionics, anionics, cationics, and amphoterics) that demonstrate thinning activity when combined with GA$_3$. These include Silwet L-77 (nonionic; polyalkyleneoxide modified polydimethylsiloxane), Aerosol TO (anionic: sodium dioctyl sulfosuccinate), Mazeen C-5 (cationic; polyoxyethylene (5) coco amine), and Mafo CB-40 (amphoteric; coco betaine).

EXAMPLE 7

Perlette Seedless grape clusters were treated as described in EXAMPLE 1, using the compositions listed in Table VII, at a bloom stage of 50-100% full bloom. The results are shown in Table VII.

TABLE VII

| Treatment | # Normal Berries per cm Lateral | Percent of UTC |
|---|---|---|
| Untreaded control (UTC) | 6.2 (1.3)$^z$ | 100 |
| 10 ppm GA$_3$ | 4.6 (1.9) | 74 |
| 10 ppm GA$_3$ + 0.5% Triton B-1956 | 4.2 (0.9) | 68 |
| 10 ppm GA$_3$ + 0.25% Tween 80 | 3.3 (0.8) | 53 |
| 10 ppm GA$_3$ + 0.25% Tween 20 | 3.1 (0.9) | 50 |

$^z$means of 12 to 16 laterals (2nd and 3rd true laterals taken from 6 to 8 clusters) with standard deviations in parentheses.

The results shown in Table VII illustrate that combinations of GA$_3$ and either 0.25 percent Tween 20 (polyoxyethylene (20) sorbitan monolaurate) or 0.25 percent Tween 80 (polyoxyethylene (20) sorbitan monooleate) demonstrated greater thinning activity (i.e., less berries per cm lateral) than GA$_3$ alone or GA$_3$ plus 0.5 percent Triton B-1956 (the traditional spray tank formulation).

The foregoing description and the EXAMPLES are intended as illustrative and are not to be taken as limiting. Still other variations within the spirit and scope of this invention are possible and will readily present themselves to those skilled in the art.

We claim:
1. A method for thinning Perlette Seedless grape cluster comprising applying a grape cluster thinning effective amount of a gibberellin and a surfactant to said grape clusters during the bloom period of said grapes, the surfactants selected from nonylphenoxypolyethoxyethanol, octylphenoxypolyethoxyethanol, trimethylnonlypolyethoxyethanol, sodium dioctyl sulfosuccinate, polyoxyethylene (5) coco amine, coco betaine, polyalkyleneoxide modified polydimethylsiloxane, polyoxyethylene (20) sorbitan monolaurate and polyoxyethylene (20) sorbitan monooleate.

2. The method of claim 1, wherein said surfactant is present at a concentration of about 0.1 to about 1.0 percent weight by volume, and said gibberellin is present at a concentration of about 5 to about 25 parts per million.

* * * * *

UNITED STATES PATENT AND TRADEMARK OFFICE
CERTIFICATE OF CORRECTION

PATENT NO. : 5,163,993

DATED : Nov. 17, 1992

INVENTOR(S) : Warren E. Shafer, Libertyville; Bala N. Devisetty, Buffalo Grove, both of Ill.

It is certified that error appears in the above-identified patent and that said Letters Patent is hereby corrected as shown below:

Column 1, Line 49, Delete ---Giberella---, Insert "Giberella"

Column 2, Line 51, Delete ---heavierberriers---, Insert "heavier berries"

Column 2, Line 52, Delete ---8:60---, Insert "8:60"

Column 2, Line 64, Delete ---Harvana---, Insert "Haryana"

Column 3, Line 15, Delete ---sufactant---, Insert "surfactant"

Column 3, Line 33, Delete ---mono-laurate---, Insert "mono laurate"

Column 3, Line 50, Delete ---Del.---, Insert "DE"

Column 3, Line 54, Delete ---Pa.---, Insert "PA"

Column 3, Line 55, Delete ---N.J.---, Insert "NJ"

Column 3, Line 59, Delete ---Del.---, Insert "DE"

Column 3, Line 62, Delete ---TO-100---, Insert "OT-100"

Column 3, Line 63, Delete ---sulfasuccinate---

Column 3, Line 65, Delete ---Ill.---, Insert "IL"

Column 4, Line 6, Delete ---entgibberellane---, Insert entgibberellane"

Column 6, Line 50, Delete ---Pa.---, Insert "PA"

Column 7, Line 16, Delete ---oxtyl---, Insert "octyl"

UNITED STATES PATENT AND TRADEMARK OFFICE
CERTIFICATE OF CORRECTION

PATENT NO. : 5,163,993

Page 2 of 3

DATED : Nov. 17, 1992

INVENTOR(S) : Warren E. Shafer, Libertyville; Bala N. Devisetty, Buffalo Grove, both of Ill.

It is certified that error appears in the above-identified patent and that said Letters Patent is hereby corrected as shown below:

Column 8, Line 5, Delete ---GAF Corp., Wayne, NY:---
  Insert "GAF Corp., Wayne, NY:"

Column 8, Line 6, Delete ---Mazer Chemicals Ltd., Gurnee, IL:---
  Insert "Mazer Chemicals Ltd., Gurnee, IL:"

Column 8, Line 12, Delete ---Union Carbide Corp., Danbury, CT:---
  Insert "Union Carbide Corp., Danbury, CT:"

Column 8, Line 14, Delete ---Rohm and Haas, Philadelphia, PA:---
  Insert "Rohm and Haas, Phiadelphia, PA:"

Column 8, Line 15, Delete ---American Cyanamid, Wayne, NJ:---
  Insert "American Cyanamid, Wayne, NJ:"

Column 8, Line 16, Delete ---Stepan Co., Northfield, IL:---
  Insert "Stepan Co., Northfield, IL:"

Column 8, Line 17, Delete ---Miller Chemical Co., Chicago, IL:---
  Insert "Miller Chemical Co., Chicago, IL:"

Column 8, Line 18, Delete ---p---, Insert "p"

Column 8, Line 25, Delete ---TO---, Insert "OT-100"

Column 8, Line 36, Delete ---untreaded---, Insert "untreated"

UNITED STATES PATENT AND TRADEMARK OFFICE
CERTIFICATE OF CORRECTION

PATENT NO. : 5,163,993
DATED : November 17, 1992
INVENTOR(S) : Warren E. Shafer, et. al.

It is certified that error appears in the above-indentified patent and that said Letters Patent is hereby corrected as shown below:

Column 8, Line 56, Delete ---cluster comprising---
                   Insert "clusters comprising"

Signed and Sealed this

Twenty-sixth Day of April, 1994

Attest:

BRUCE LEHMAN

Attesting Officer     Commissioner of Patents and Trademarks